(12) United States Patent
Moellendorf et al.

(10) Patent No.: US 6,407,479 B1
(45) Date of Patent: Jun. 18, 2002

(54) SENSOR ARRANGEMENT FOR DETECTING THE PHYSICAL PROPERTIES OF LIQUIDS

(75) Inventors: Manfred Moellendorf, Leonberg; Heinz Eisenschmid, Hirschlanden; Falk Herrmann, Leonberg, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/831,055

(22) PCT Filed: Oct. 28, 1999

(86) PCT No.: PCT/DE99/03457

§ 371 (c)(1),
(2), (4) Date: May 4, 2001

(87) PCT Pub. No.: WO00/26660

PCT Pub. Date: May 11, 2000

(30) Foreign Application Priority Data

Nov. 4, 1998 (DE) .......................... 198 50 802

(51) Int. Cl.⁷ .................................. H03H 9/19
(52) U.S. Cl. .................................. 310/313 A
(58) Field of Search ................ 310/313 R, 313 A

(56) References Cited

U.S. PATENT DOCUMENTS

| | | | |
|---|---|---|---|
| 5,076,094 A | * 12/1991 | Frye et al. | 310/313 B |
| 5,130,257 A | * 7/1992 | Baer et al. | 204/403 |
| 5,216,312 A | * 6/1993 | Baer et al. | 310/313 D |
| 5,440,188 A | 8/1995 | Krempl | 310/313 A |
| 5,741,961 A | 4/1998 | Casaus | 73/32 R |
| 5,910,286 A | * 6/1999 | Lipskier | 422/68.1 |
| 6,304,021 B1 | * 10/2001 | Wolf et al. | 310/313 B |

FOREIGN PATENT DOCUMENTS

EP 0 392 879 A 10/1990 ............ H03H/9/25

OTHER PUBLICATIONS

Du J. et al: A Study of Love–Wave Acoustic Sensors Sensors and Actuators, A, CH, Elsevier, Sequoia S.A., Alusanne, vol. A56, No. 3, Sep. 1, 1996, pp. 211–219.

* cited by examiner

Primary Examiner—Thomas M. Dougherty
(74) Attorney, Agent, or Firm—Michael J. Striker

(57) ABSTRACT

A sensor arrangement for ascertaining physical properties of a liquid is proposed, having electro-acoustical converters (6) on a substrate (5) which are wettable with the liquid and are suitable for generating and detecting acoustical surface waves with predetermined wave modes. A Y-rotated quartz slice is used as the substrate (5), and above the substrate (5) is a waveguide layer (16); the standard of the Y rotation of the quartz slice and the material of the waveguide layer (16) are selected such that an extensive temperature compensation within the range of temperature of the liquid to be investigated is obtained.

6 Claims, 2 Drawing Sheets

SENSOR ARRANGEMENT FOR DETECTING THE PHYSICAL PROPERTIES OF LIQUIDS

BACKGROUND OF THE INVENTION

The invention relates to a sensor arrangement for ascertaining physical properties of liquids.

By way of example, sensor arrangements with so-called acoustical SAW or surface wave components (SAW=surface acoustic wave) are used as sensors for the most various physical properties in liquids. One important field in this respect is measuring electrical variables, such as the dielectric constant and/or the conductivity, measuring mechanical variables, such as the density and/or the viscosity, and the investigation of chemical properties, such as the presence of special substances in liquids.

In a known sensor arrangement, the starting point is a measurement principle that is described for instance in the paper entitled "A study of Love-wave acoustic sensors", by J. Du, G. L. Hardling, P. R. Ogilvy and M. Lake, in the professional journal Sensors and Actuators A56 (1996), pages 211–219. With the measurement structure described here, a sensor has been achieved in which horizontally polarized acoustic shear waves are used, so-called leaky waves or surface skimming bulk waves (SSBWs), or Love-waves. These acoustical wave modes are generated and also detected with so-called interdigital transducers, known per se from the aforementioned prior art, so that from the propagation behavior over a propagation or measurement path, the desired sensor signal can be obtained.

Depending on the measurement construction required, various materials and arrangements for the sensor elements are used, such as a certain substrate material for the sensor elements, a predetermined wave propagation direction, optionally also a special layer construction on the substrate material, and a certain arrangement of the sensor elements, constructed as electro-acoustical converters. One or more of the aforementioned acoustic wave modes, known per se, occur here; they differ in terms of a possible measurement sensitivity, propagation speed, an acoustoelectrical coupling factor, and a vulnerability to shear effects, and so forth and thus determine the suitability of a special sensor type for a specific measurement task.

The above-described acoustic wave modes, known from the prior art, as noted involve horizontally polarized acoustic shear waves, in which a wave propagating along the surface of the substrate on which the electro-acoustical converters are located is utilized.

Besides the measurement sensitivity when SAW components are used as sensors, especially for investigating liquids, the influence of the temperature on the measurement outcome is also especially significant; for instance in use in liquid media, of the kind employed in the automotive field (such as oils, fuels, brake fluid, and so forth), a relatively wide temperature range affecting the measurement outcome occurs, ranging between −40° C. and +150° C.

SUMMARY OF THE INVENTION

The sensor arrangement referred to at the outset for ascertaining physical properties of liquids is advantageously refined according to the invention, as defined by the characteristics of the body of the main claim.

This sensor arrangement according to the invention advantageously has a Y-rotated quartz slice and above the substrate it has a waveguide layer; the Y rotation of the quartz slice and the material of the waveguide layer are selected such that extensive temperature compensation in the range of temperature of the liquid is obtained. In the case of the wave modes mentioned at the outset for the acoustical surface wave, use can be made of the effect that the acoustic wave guidance through an acoustically slow waveguide layer located on the substrate is influenced in such a way that horizontally polarized, near-surface shear waves (SSB waves) or leaky waves. This purposefully enhances or exactly sets the measurement sensitivity to viscous, acoustoelectrical or gravimetric interactions with the ambient liquid.

A precondition for a pronounced waveguide effect is the greatest possible difference between the shear wave speeds of the substrate and the waveguide layer.

For instance with SAW components used in filter technology, so-called ST slices of α quartzes, rotated for instance by 42.75° about the crystallographic X axis are used. On this quartz slice, with the aid of interdigital transducers known from the prior art mentioned at the outset, SSB waves can be excited along the rotated Z propagation direction. By utilizing the aforementioned effect of acoustical wave guidance through acoustically slow dielectric layers, these modes can be converted into Love modes.

The temperature coefficient of the Love mode waves in the measurement arrangement cited at the outset as prior art is approximately +30 ppm/K. Since the frequency fluctuations expected for sensor applications without temperature stabilization are on the same order of magnitude as the measurement effects, according to the invention the temperature coefficient at the working temperature of the liquid is reduced by at least one order of magnitude.

In a first advantageous embodiment, a Y-rotated quartz slice with angles of rotation between 25° and 36° is used as the substrate, and an SiO2 layer is used as the waveguide layer. These quartz slices with angles of rotation between 25° and 36° are especially suitable, because with them in conjunction with SiO2 layers of typical thickness (0.01 to 0.25 acoustical wavelengths), temperature-compensated systems with working temperatures between −40° C. and +150° C. can be produced. Furthermore, the SSB waves of these quartz slices have the high phase speeds and coupling factors that are required for Love mode sensors.

In a second embodiment, a Y-rotated quartz slice with angles of rotation between 40° and 60° is used as the substrate, and a layer with a negative temperature coefficient, preferably a polymer layer, is used as the waveguide layer. Waveguide layers with a negative temperature coefficient, such as polymers of PMMA, BCB, ormocers or spin-on glass, in conjunction with a Y-rotated quartz slice, lead to a parabolic temperature dependency of the resultant Love mode waves and thus to a so-called turnover temperature that is shifted in the direction of lower temperatures.

This effect can thus be utilized, as in the first embodiment, to generate a temperature-compensated system that simultaneously has good sensor properties. For each of these quartz slices, for a given wave guide material, precisely one layer thickness exists at which the resultant Love mode component has first order temperature compensation at the intended working temperature.

In a third embodiment, a Y-rotated quartz slice, especially with an angle of rotation of approximately 48°, is used as the substrate, and a layer with a virtually linear negative temperature coefficient, such as a polymer layer, is used as the waveguide layer. This quartz slice of the substrate has a quadratic temperature coefficient that tends toward zero, so that in conjunction with a layer with a linear negative temperature coefficient, given a choice of the correct layer thickness, a sensor arrangement can be produced with first and second order temperature compensation in a good approximation. Furthermore, at the layer thicknesses required for the temperature compensation, these arrangements exhibit very high sensitivities to viscous and gravimetric interactions, making them especially well suited for sensor use.

In an especially advantageous application, the sensor arrangement is used in a motor vehicle to determine the quality of the motor oil or operating liquids, and the substrate can be dipped directly into the oil to be measured.

These and other characteristics of preferred refinements of the invention are disclosed not only in the claims, including the dependent claims, but also in the description and the drawings; each of the individual characteristics can be realized alone or several can be combined in the form of subcombinations in the embodiment of the invention and realized in other fields, and can represent advantageous versions that are patentable on their own, and for these versions patent protection is claimed here:

BRIEF DESCRIPTION OF THE DRAWINGS

One exemplary embodiment of the sensor arrangement according to the invention will be explained in conjunction with the drawing. Shown are.

DESCRIPTION OF THE PREFERRED EMBODIMENT

Figure 1:
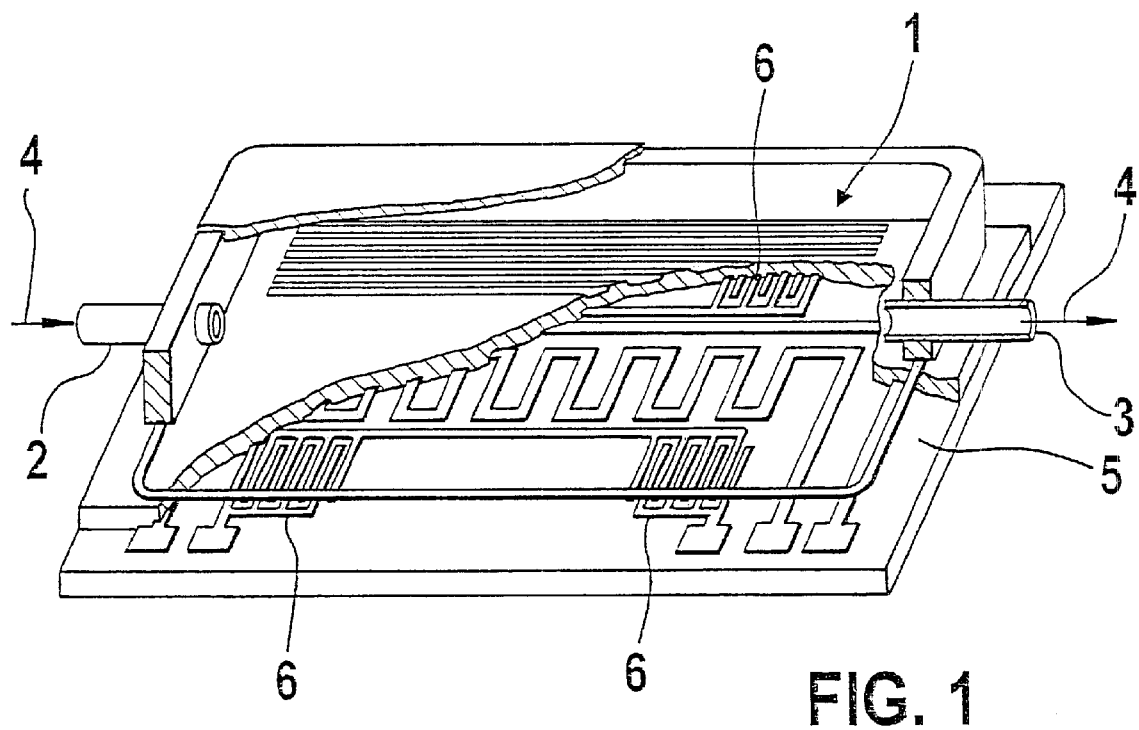
FIG. 1, a schematic view of a sensor arrangement for acertaining the density and viscosity of a liquid flowing through the sensor arrangement.

From FIG. 1, a sensor arrangement 1 is shown in a basic cutaway view as an example of the application of the invention; a measurement liquid flows through it from an entrance 2 to an exit 3 in the direction of the arrow 4, so that the density and viscosity of the liquid can be determined. The primary component of the proposed sensor arrangement 1 is a substrate 5, polished on one side, of a piezoelectric material, in which horizontally polarized acoustic shear modes of basic sensor elements can be excited and are capable of propagation. As substrate materials, Y- rotated quartz slices, some lithium niobate and lithium tantalate slices, and suitably polarized piezoelectric ceramics are suitable.

An arrangement of metal interdigital transducers (IDTs) 6 is located on the polished surface of the a substrate 5. These interdigital transducers 6 serve to excite and detect the acoustical surface waves.

Figure 2:
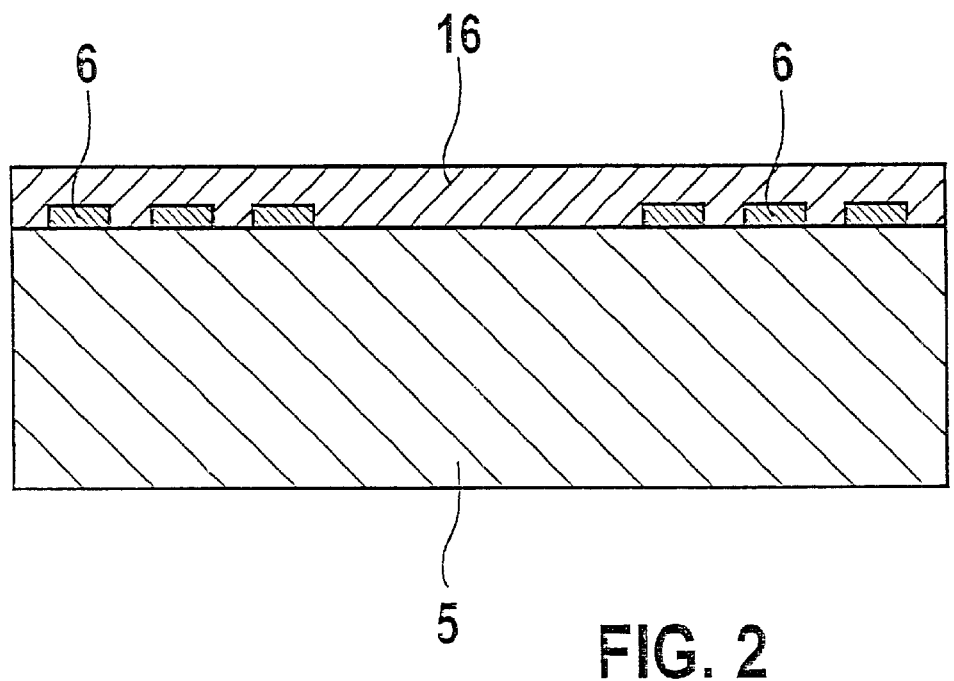
FIG. 2, a detailed section through a substrate with interdigital transducer as an electro-acoustical converter and with a waveguide layer located above it.

On the substrate 5 in FIG. 1 and in the detail view of FIG. 2 above the basic sensor elements having the interdigital transducers 6, there is an acoustic waveguide layer 16, which for example can comprise an ormocer, a silicon compound, or a polymer, so that the general shear mode (leaky wave or SSBW) of the acoustic wave becomes a so-called waveguide mode (in this case a Love mode wave).

By a suitable choice of the materials of the substrate 5 and waveguide layer 16 in accordance with FIGS. 1 and 2, an optimal temperature compensation in the sensor arrangement can be achieved; in particular, the temperature behavior of the acoustic wave modes can be optimized, at an operating temperature, for example of approximately 25°, or at some other temperature in the range from −40° to +150° C. The temperature behavior of these wave modes has a parabolic course; one goal of the choice of material is to place the apex of the temperature curve (the turnover temperature) at the operating temperature, so that the temperature change will have the least possible influence on the oscillation frequency of the arrangements. The temperature coefficient of a Love mode wave can be described by a superposition of the temperature coefficients of the substrate 5 and of the waveguide layer 16. Given a correct choice of the substrate and layer material, the temperature behavior can thus be optimized.

Figure 3:
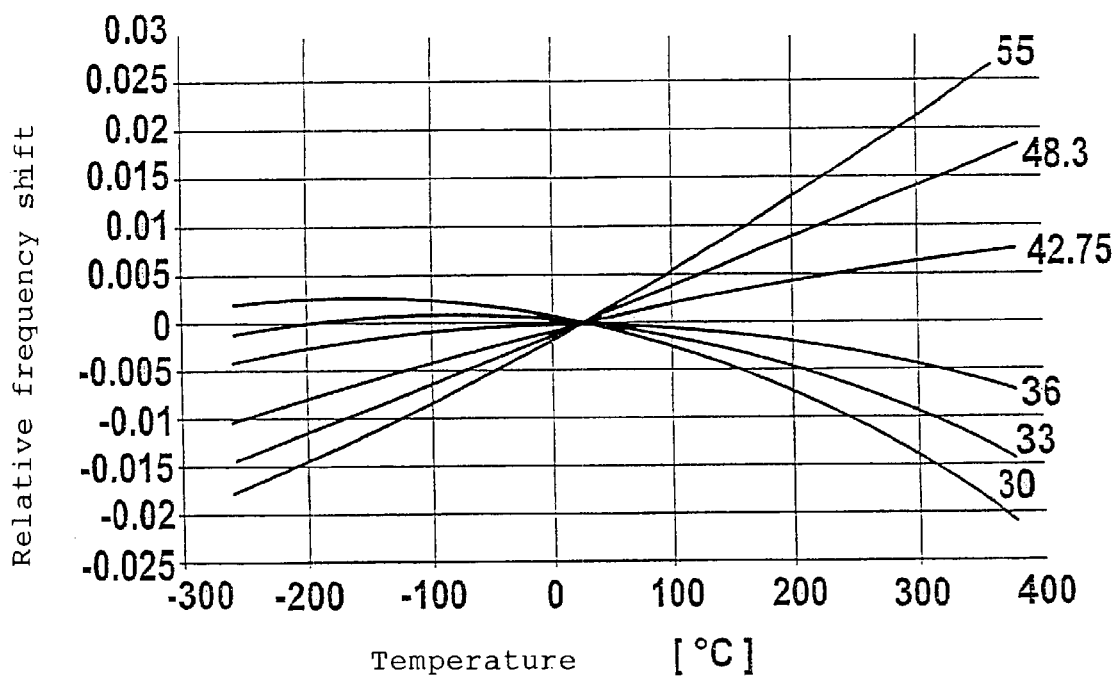
FIG. 3, a graph showing the temperature responses of S waves on various quartz slices of the substrate.

The temperature behavior of the wave modes mentioned is shown in FIG. 3 for various Y-rotated quartz slices (in the range from 30° to 55°), expressed here by the frequency shift standardized to the operating temperature, usually 25°C.; the temperature behavior has a parabolic course.

Figure 4:
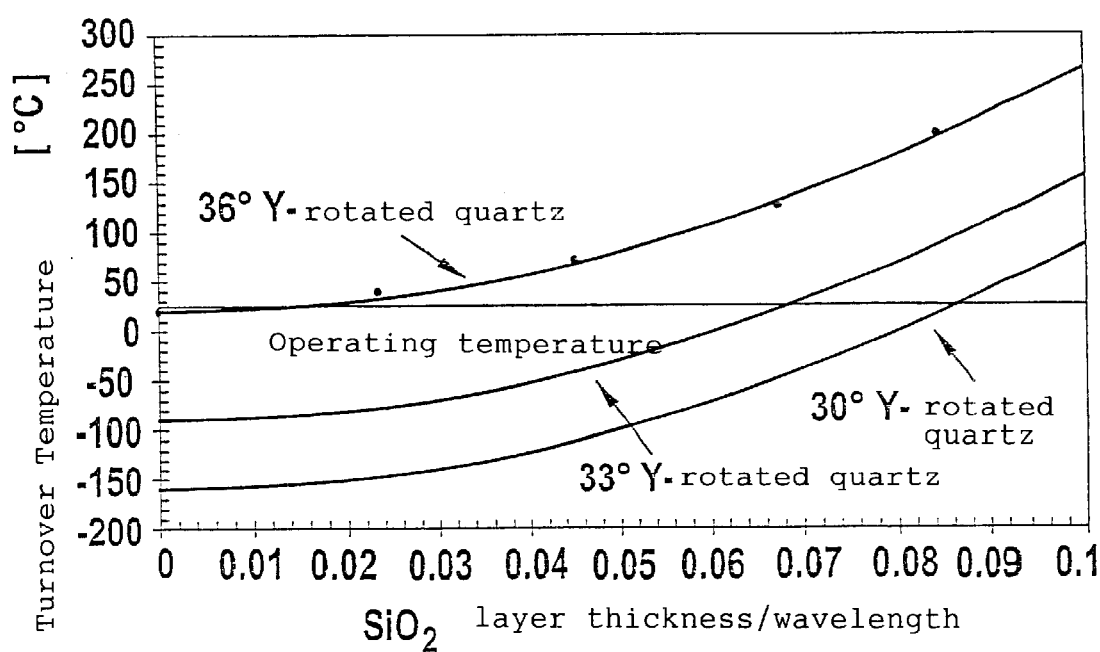
FIG. 4, a graph showing the so-called turnover temperature of Love mode waves as a function of the layer thickness of the waveguide layer.

As the substrate 5, a Y-rotated quartz slice can for instance be used, especially with angles of rotation between 25° and 36°, and as the waveguide layer 16, an SiO2 layer can be used, whose thickness is selected in accordance with the required sensitivity. In the range of a working temperature of −40° to +150°, a first order temperature-compensated system is obtained. An SiO2 layer, in contrast to many other materials, has a positive, virtually linear temperature coefficient. If such a layer is used on a Y-rotated quartz slice to generate Love mode waves, then the temperature response of the resultant modes, like that of the fundamental SSB wave, is parabolic, but with a turnover temperature that is shifted in the direction of higher temperatures. How greatly the turnover temperature is shifted depends on the layer thickness referred to the acoustic wavelength. This relationship is shown in FIG. 4 for the quartz slices having a Y rotation of 30°, 33°, and 36°.

If a quartz slice is used in which the turnover temperature of the SSB wave is markedly below the operating temperature, then in conjunction with an SiO2 layer, the turnover temperature of the Love mode wave can be shifted to the operating temperature, which is equivalent to a first order compensation of the temperature coefficient. The extent of the turnover temperature shift depends, as FIG. 4 shows, on the standardized waveguide layer thickness, which in turn determines the sensitivity of the Love mode sensor. For every waveguide layer thickness and working temperature determined by the special sensor function, a quartz slice can be found that leads to a temperature-compensated sensor element.

In another example, a Y-rotated quartz slice, especially with angles of rotation between 40° and 60°, can be used as the substrate 5, and a layer with a negative temperature coefficient, whose thickness is selected to suit the required sensitivity, can be used as the waveguide layer 16. Once again, in the range of a working temperature of −40° to +150°, a first order temperature-compensated system is obtained.

In a third example, as the substrate 5, a Y-rotated quartz slice with an angle of rotation of 48°±1°, can be used as the substrate 5, and as the waveguide layer 16, a layer with a virtually linear negative temperature coefficient can be used, whose thickness is selected to suit the required sensitivity.

The result in the range of a working temperature of −40° to +150° is a first and second order temperature-compensated system.

What is claimed is:

1. A sensor arrangement for ascertaining physical properties of a liquid, comprising a substrate; electro-acoustical convertors applied to said substrate and operatively connected to a liquid, said convertors being formed for generating and detecting acoustical surface waves embodied as Love-waves, so that a propagation behavior of the Love-waves along a measurement path can be ascertained as a standard for physical properties, said substrate being formed as Y-rotated quartz slice; and a wave guide layer exposed above said substrate, a standard of the Y rotation of said quartz slice and a material of said wave guide layer being selected so that an extensive temperature compensation of the Love-waves employed is obtained within a range of a temperature of the liquid to be investigated.

2. A sensor arrangement as defined in claim 1, wherein said Y-rotated quartz slice has an angle of rotation between 25° and 36°, said waveguide layer being composed of $SiO_2$.

3. A sensor arrangement as defined in claim 1, wherein said Y-rotated quartz slice has an angle of rotation between 40° and 60°, said waveguide layer being formed as a layer with a negative temperature coefficient.

4. A sensor arrangement as defined in claim 1, wherein said Y-rotated quartz slice has an angle of rotation of approximately 48°, said waveguide layer being formed as a layer with a virtually linear negative temperature coefficient.

5. A sensor arrangement as defined in claim 1, wherein said waveguide layer is a polymer layer.

6. A sensor arrangement as defined in claim 1, wherein said sensor arrangement is usable in a motor vehicle to determine a quality of a motor oil or operating liquids, said substrate being dipped directly into an oil to be measured.

* * * * *